United States Patent [19]

Sun

[11] 4,034,039
[45] July 5, 1977

[54] PURIFICATION OF METHYLENEDIANILINES

[75] Inventor: Kwok K. Sun, Hamden, Conn.

[73] Assignee: The Upjohn Company, Kalamazoo, Mich.

[22] Filed: May 28, 1976

[21] Appl. No.: 690,913

[52] U.S. Cl. .................. 260/570 D; 260/453 AM
[51] Int. Cl.$^2$ ........................................ C07C 87/20
[58] Field of Search ........................... 260/570 D

[56] References Cited

UNITED STATES PATENTS 3,542,871   11/1970   Thompson ..................... 260/570

Primary Examiner—Robert V. Hines
Attorney, Agent, or Firm—Denis A. Firth; John Kekich

[57] ABSTRACT

A process is described for the isolation of 4,4'-diaminodiphenylmethane in substantially pure form (of the order of purity of at least 95%) from admixtures thereof with the corresponding 2,4'-isomer and 2,2'-isomer. The isomeric mixture of diamines is heated, optionally in the presence of an inert organic solvent, with at least two equivalents, per mole of said diamine mixture, of a phenol or bisalkylidenephenol. The 4,4'-diaminodiphenylmethane forms a complex with said phenol and the 4,4'-isomer of the diamine is isolated therefrom in substantially pure form by treatment with alkali or by heating to dissociate. The isomeric mixture of diamines used as starting material can be employed in the form of a mixture of polymethylene polyphenyl polyamines containing a major portion of said diamines.

11 Claims, No Drawings

PURIFICATION OF METHYLENEDIANILINES

BACKGROUND OF THE INVENTION

1. Field of the Invention

This invention relates to a process of separating isomeric diaminodiphenylmethanes and is more particularly concerned with the isolation of substantially pure 4,4'-diaminodiphenylmethane from admixture with the corresponding 2,4'-isomer and or 2,2'-isomer.

2. Description of the Prior Art 4,4'-Diaminodiphenylmethane is a well-known compound which is useful as an intermediate in a number of reactions. For example, it is an intermediate in the preparation of polyamides such as nylon and in the preparation of the corresponding 4,4'-methylenebis(phenyl isocyanate) which latter is widely used in the preparation of polyurethane elastomers. The diamine is normally prepared by condensation of aniline and formaldehyde to yield a mixture of polymethylene polyphenyl polyamines in which the major component (40% by weight or higher) is diamine and from which the latter is isolated by, for example, distillation. The diamine so prepared is generally a mixture of the 4,4'-isomer in association with varying amounts of 2,4'-isomer and some 2,2'-isomer depending upon the particular method employed in its manufacture; see, for example U.S. Pat. Nos. 3,362,979; 3,676,497 and 3,857,890.

For the various uses of 4,4'-diaminodiphenylmethane discussed above it is generally necessary to employ the compound in a substantially pure form. By "substantially pure" is meant that the diamine contains less than about 5 percent by weight, and preferably less than about 2 percent by weight, of the corresponding 2,4'-isomer and or 2,2'-isomer. Various methods of achieving such a purity have been described. A commonly used method is fractional distillation under reduced pressure which normally involves some overall loss of material due to decomposition, polymerization and the like reactions which occur because of prolonged exposure to heat in the distillation kettle.

Canadian Pat. No. 745,173 describes the isolation of 4,4'-diaminodiphenylmethane in substantially pure state from the crude reaction product derived by condensation of aniline and formaldephyde in the presence of hydrochloric acid. The latter product is diluted with hot water and partially neutralized with alkali whereupon the substantially pure monohydrochloride of 4,4'-diaminodiphenylmethane crystallizes out upon cooling of the product. Because of the large volumes of solution required and other factors, the process is not suitable for use in a continuous commercial operation.

British Specification 1,169,127 describes the separation of 4,4'-diaminodiphenylmethane from admixture with its isomers by treating the mixture with an alkali metal or alkaline earth metal halide, cyanide or isothiocyanate, with which the 4,4'-isomer selectively forms an adduct, separating the adduct so formed, and regenerating the 4,4'-isomer from the adduct by heating with water or an inert solvent. Removal of last traces of the salt used to form the adduct is one of the drawbacks of this procedure which is not readily adaptable to commercial operation.

We have now found that the 4,4'-isomer of diaminodiphenylmethane can be readily separated from the corresponding 2,4'- and or 2,2'-isomers by a simple procedure which is readily adaptable to commercial production and which is free from the disadvantages noted above.

SUMMARY OF THE INVENTION

This invention comprises a process for separating 4,4'-diaminodiphenylmethane from admixtures thereof with the corresponding 2,4'-isomer which process comprises:

heating said mixture of isomeric diamines at a temperature of 30° C to 150° C with a phenol selected from the class consisting of phenol, lower-alkyl-substituted phenols, lower-alkoxy-substituted phenols, catechol, resorcinol and bis-lower-alkylidene phenols, said phenol being in an amount such that there is at least one phenolic hydroxyl for each amino group in said 4,4'-diaminodiphenylmethane;

separating the complex of 4,4'-diamino-diphenylmethane and said phenol so formed; and regenerating substantially pure 4,4'-diaminodiphenylmethane from said complex.

The term "lower-alkyl" is used throughout this specification and claims as meaning alkyl from 1 to 6 carbon atoms such as methyl, ethyl, propyl, butyl, pentyl, hexyl and isomeric forms thereof. The term "lower-alkoxy" is used through this specification and claims as meaning alkoxy from 1 to 6 carbon atoms such as methoxy, ethoxy, propoxy, butoxy, pentyloxy, hexyloxy and isomeric forms thereof. The term "bis-alkylidene phenols" as used throughout this specification and claims means a compound of the formula

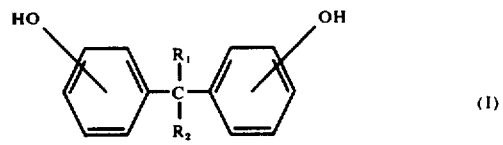

(I)

wherein $R_1$ and $R_2$ each individually represent lower-alkyl as defined above.

DETAILED DESCRIPTION OF THE INVENTION

In carrying out the process of the invention, the mixture of isomeric diamines is heated with the phenol, optionally in the presence of an inert organic solvent. By "inert organic solvent" is meant an organic solvent which does not itself enter into reaction with any of the reactants or interfere in any other way with the desired course of the reaction. Illustrative of inert organic solvents are benzene, toluene, xylene, chlorobenzene, decalin, carbon tetrachloride, cyclopentane, cyclohexane, and the like. Advantageously, the inert organic solvent is one having a boiling point higher than that of the phenol employed.

The phenol, whichever of those set forth above is employed, is always present in an amount such that there is at least one phenolic hydroxyl group for each amino group in the 4,4'-diaminodiphenylmethane. Where the phenol employed is phenol itself, it is found advantageous to employ a substantial excess over the amount specified above and to use the excess phenol, in the molten state, as solvent for the reaction. In the case of most of the other phenols, it is preferred to use an inert organic solvent as the reaction medium.

The mixture of isomeric diamines and the phenol, and optionally the inert organic solvent, is heated advantageously at a temperature in the range of about 30° C to about 150° C and preferably in the range of about 50° C to about 100° C. The complex so formed is a crystalline compound which separates from the reaction mixture upon cooling to room temperature and can be readily isolated therefrom by centrifugation, filtration and like techniques. Where the phenol employed is a monhydric phenol, the resulting complex is one in which the phenol and diamine are present in the molar proportions of 2:1. Where the phenol employed is a dihydric phenol, the resulting complex is one in which the phenol and diamine are present in the molar proportions of 1:1.

The complex so formed and isolated contains diamine in a form which is substantially pure 4,4'-diaminodiphenylmethane. By "substantially pure" is meant that the 4,4'-isomer of the diamine contains at least 95 percent by weight and preferably at least 98 percent by weight of said isomer the remainder of said product being the corresponding 2,4'-isomer and or 2,2'-isomer. The free diamine, still in substantially pure form, can be isolated from the complex with the phenol in various ways. For example, where the phenol is one which is volatile, such as phenol itself, it is merely necessary to heat the complex to a temperature which is above the dissociation temperature of the complex but below about 170° C and to remove the phenol by distillation under reduced pressure. Alternatively, all of the various complexes can be decomposed by treating with excess dilute aqueous alkali metal hydroxide solution, such as sodium hydroxide, potassium hydroxide and the like, to liberate the free diamine. The phenol passes into solution and the diamine remains as an insoluble solid which can be isolated by centrifugation, filtration, and the like.

The residue which remains after the separation of the above complex from the primary reaction product contains diamine which is richer in the 2,4'-isomer than the mixture of isomeric diamines which was employed as starting material. This mixture of diamines can be isolated from the residue and the diamine so recovered can then be recycled through the process of the invention to isolate more pure 4,4'-isomer therefrom.

The phenols which are employed in the process of the invention include phenol itself; lower-alkyl substituted phenols such as o-cresol, m-cresol, p-cresol, ethylphenol, butylphenol, hexylphenol, 1,3,4-xylenol and the like; lower-alkoxy-substituted phenols such as guaiacol, hydroquinone monomethyl ether, hydroquinone monobutyl ether, hydroquinone monohexyl ether and the like; dihydric phenols such as hydroquinone, resorcinol, orcinol and the like; and biasalkylidene phenols of the formula (I) above such as 2,2-di(4-hydroxyphenyl)-propane[Bisphenol A], 1,1-di(4-hydroxyphenyl)propane, 3,3-di(3-hydroxyphenyl)pentane, 2,2-di(4-hydroxyphenyl)-butane[Bisphenol B], and the like.

The process of the invention, in addition to being useful in separating the 4,4'-isomer from admixture with the isomeric diamines per se, can also be applied to the separation of 4,4'-isomer from the isomeric diamines which are present as part of a mixture of polymethylene polyphenyl polyamines obtained by condensation of aniline and formaldehye; see the art cited above. Advantageously, said polymethylene polyphenyl polyamines contain at least about 20 percent by weight of diamine and preferably contain from about 70 percent to about 99 percent by weight of diamine.

The following examples describe the manner and process of making and using the invention and set forth the best mode contemplated by the inventor of carrying out the invention but are not to be construed as limiting.

EXAMPLE 1

A mixture of 3.96 g. (20 mmol.) of a mixture of diaminodiphenylmethanes (containing 83.7 percent by weight of 4,4'-isomer and 16.3 percent by weight of 2,4'-isomer) and 28.2 g. (300 mmol.) of phenol was heated at 90° C, with stirring, for 5 minutes and was then cooled to room temperature (circa 20° C). The solid which crystallized was isolated by filtration, washed with water and dried. There was thus obtained a 2:1 molar complex of phenol and 4,4'-diaminodiphenylmethane having a melting point of 56° C. The complex was heated to 170° C at a pressure of 0.05 mm. of mercury and maintained thereat until no further phenol distilled over. The residue (0.174 g.:4.4% yield) was found by vapor phase chromatography to be 100 percent 4,4'-diaminodiphenylmethane containing no detectable amounts of 2,4'-isomer.

The filtrate from the isolation of the above complex was distilled at 170° C and a pressure of 0.05 mm. of mercury to remove phenol and leave a residue (3.51 g.:88.6 percent recovery) of diamine which was found by vapor phase chromatography to contain 78.4 percent by weight of 4,4'-isomer and 21.6 percent by weight of 2,4'-isomer. The water washing from the isolation of the above complex was extracted with chloroform and the chloroform extract was evaporated and heated to 170° C/0.05 mm. to obtain 0.41 g. (10.4 percent recovery) of diamine which was found by vapor phase chromatography to contain 99.1 percent by weight of 4,4'-isomer and 0.9 percent by weight of 2,4'-isomer.

EXAMPLE 2

The process described in Example 1 was repeated but the molar proportion of phenol to diamine was reduced from 15:1 to 3:1 as follows.

A mixture of 3.0 g. (15.2 mmol.) of a mixture of diaminodiphenylmethanes (containing 85.5 percent of 4,4'-isomer and 14.5 percent of 2,4'-isomer) and 4.23 g. (45 mmol.) of phenol was heated at 90° C, with stirring, for 5 minutes and was then cooled to room temperature (circa 20° C). The reaction product was worked up exactly as described in Example 1. The 2:1 molar complex of phenol and 4,4'-diaminodiphenylmethane, after isolation, was distilled at 170° C and 0.05 mm. of mercury to remove phenol and leave a residue of 2.37 g. (79 percent recovery) of diamine which was found by vapor phase chromatography to contain 96.3 percent by weight of 4,4'-isomer and 3.7 percent by weight of 2,4'-isomer. The diamine (0.42 g.:14 percent recovery), recovered by the procedure of Example 1 from the mother liquor remaining after separation of the above complex, was found, by vapor phase chromatography, to contain 43.5 percent by weight of 4,4'-isomer and 56.5 percent by weight of 2,4'-isomer. The diamine (0.22 g.:7.3 percent recovery), recovered by the procedure described in Example 1 from the aqueous washing of the above described complex, was found, by vapor phase chromatography, to contain 47.4 percent by weight of 4,4'-isomer and 52.6 percent by weight of 2,4'-isomer.

EXAMPLE 3

This Example shows the use of an inert organic solvent (cyclohexane) in the isolation of the 2:1 molar complex of phenol and 4,4'-diaminodiphenylmethane.

A mixture of 9.90 g. (50 mmol.) of a mixture of diaminodiphenylmethanes) containing 98.2 percent by weight of 4,4'-isomer and 1.8 percent by weight of 2,4'-isomer), 14.1 g. (150 mmol.) of phenol and 5.6 g. of cyclohexane was heated with stirring at 80° C for 5 mins. and then cooled to room temperature (circa 20° C). The resulting product was then worked up using the procedure described in Example 1. The 2:1 complex of phenol and 4,4'-diaminodiphenylmethane so obtained was decomposed using the procedure described in Example 1 to yield 8.93 g. (90.2 percent recovery) of diamine which was found by vapor phase chromatography to contain 99.2 percent by weight of 4,4'-isomer and 0.8 percent by weight of 2,4'-isomer. The diamine (0.53 g.:5.3 percent recovery) obtained from the mother liquor using the procedure of Example 1 was found by vapor phase chromatography to contain 17.3 percent by weight of 2,4'-isomer and 82.7 percent by weight of 4,4'-isomer.

EXAMPLE 4

This Example shows the use of another inert organic solvent (carbon tetrachloride) in the isolation of the 2:1 molar complex of phenol and 4,4'-diaminodiphenylmethane.

A mixture of 9.90 g. (50 mmol.) of the same mixture of diamines as used in Example 3, 8.0 g. (85 mmol.) of phenol and 50 ml. of carbon tetrachloride was heated with stirring under reflux for 5 minutes and then cooled to 30° - 40° C. The resulting product was worked up using the procedure described in Example 1. The 2:1 complex of phenol and 4,4'-diaminodiphenylmethane was decomposed using the procedure described in Example 1 to yield 7.80 g. (78.8 percent recovery) of diamine which was found by vapor phase chromatography to contain 99.5 percent by weight of 4,4'-isomer and 0.5 percent by weight of 2,4'-isomer. The diamine (1.99 g.:20.2 percent recovery) obtained from the mother liquor using the procedure of Example 1 was found by vapor phase chromatography to contain 8.1 percent of 2,4'-isomer and 91.9 percent of 4,4'-isomer.

EXAMPLE 5

A mixture of 3.96 g. (20 mmol.) of the same mixture of diamines employed in Example 3, 4.10 g. (18 mmol.) of Bisphenol A and 20 ml. of monochlorobenzene was heated at 80° C with stirring for 5 minutes and then cooled to room temperature (circa 20° C). The crystalline 1:1 molar complex of Bisphenol A and 4,4'-diaminodiphenylmethane which separated was isolated by filtration and washed with chlorobenzene on the filter before being dried in vacuo. The complex had a melting point of 85.5° to 87° C. The complex was decomposed by heating at 80° C in the presence of excess 0.5N aqueous sodium hydroxide solution and the free amine which separated was insoluble in the dilute alkali solution and was isolated by filtration, washed with water and dried. There was thus obtained 3.48 g. (88 percent recovery) of diamine which was found by vapor phase chromatography to contain 99.8 percent by weight of 4,4'-isomer and 0.2 percent by weight of 2,4'-isomer. The free Bisphenol A, which was dissolved in the dilute alkali solution, was recovered by cooling the solution to 0° C. The mother liquor of the complex which was recovered from the latter filtration was evaporated to yield 0.6 g. (15.2 percent recovery) of diamine which was found by vapor phase chromatography to contain 12.5 percent by weight of 2,4'-isomer and 87.5 percent by weight of 4,4'-isomer.

EXAMPLE 6

A mixture of 4.7 g. (50 mmol.) of phenol and 1.997 g. (10.1 mmol.) of a mixture of diaminodiphenylmethanes containing 49.6 percent by weight of the 4,4'-isomer and 50.4 percent by weight of the 2,4'-isomer was heated at 90° C for 1 hour with stirring and was then cooled to 0° C. The solid which crystallized was isolated by filtration, washed with ether, and dried. The 2:1 molar complex of phenol and 4,4'-diaminodiphenylmethane so obtained was heated to 170° C at a pressure of 0.05 mm. of mercury and maintained thereat until no further phenol distilled over. The residue (0.702 g.:35.2 percent yield) was found by vapor phase chromatography to contain 95.6 percent by weight of 4,4'-diaminodiphenylmethane and 4.4 percent by weight of 2,4'-diaminodiphenylmethane.

The filtrate from the isolation of the above complex was worked up as described in Example 1 to obtain 1.19 g. (59.6 percent yield) of diamine which was found, by vapor phase chromatography, to contain 25.4 percent by weight of 4,4'-diaminodiphenylmethane and 74.6 percent by weight of 2,4'-diaminodiphenylmethane. A further 0.13 g. (6.5 percent recovery) of diamine was isolated from the water washings employed in isolation of the latter material as described in Example 1. This diamine was found, by vapor phase chromatography, to contain 52.2 percent by weight of 4,4'-isomer and 47.8 percent by weight of 2,4'-isomer.

I claim:

1. A process for the separation of 4,4'-diaminodiphenylmethane in substantially pure form from admixtures thereof with the corresponding 2,4'-isomer and 2,2'-isomer, which process comprises:

heating said mixture of isomeric diamines at a temperature of 30° C to 150° C with a phenol selected from the class consisting of phenol, lower-alkyl substituted phenols, lower-alkoxy substituted phenols, catechol, orcinol, resorcinol and bis-lower-alkylidene phenols, said phenol being employed in an amount such that there is at least one phenolic hydroxyl for each amine group in said 4,4'-diaminodiphenylmethane;

separating the complex of 4,4'-diaminodiphenylmethane and said phenol so formed; and regenerating substantially pure 4,4'-diaminodiphenylmethane from said complex.

2. The process of claim 1 wherein said reaction of isomeric diamines with said phenol is conducted in the presence of an inert organic solvent.

3. The process of claim 1 wherein said complex of said phenol and 4,4'-diaminodiphenylmethane is treated with alkali to regenerate the substantially pure 4,4'-diaminodiphenylmethane.

4. The process of claim 1 wherein said phenol is phenol itself and the substantially pure 4,4'-diaminodiphenylmethane is regenerated from said complex by heating and distilling away the phenol under reduced pressure.

5. The process of claim 1 wherein said phenol is Bisphenol A.

6. A process for the separation of 4,4'-diaminodiphenylmethane in substantially pure form from admixtures thereof with the corresponding 2,4'-isomer and 2,2'-isomer which process comprises:
heating said mixture of isomeric diamines with at least two moles, per mole of said mixture of diamines, of molten phenol;
separating from the reaction mixture the solid complex of phenol and 4,4'-diaminodiphenylmethane so formed; and
heating said complex in vacuo at a temperature above its dissociation point to remove said phenol and leave substantially pure 4,4'-diaminodiphenylmethane.

7. The process of claim 6 wherein said mixture of isomeric diamines comprises a mixture of diamines and oligomeric polymethylene polyphenyl polyamines obtained by the condensation of aniline and formaldehyde.

8. A process for the separation of 4,4'-diaminodiphenylmethane in substantially pure form from admixtures thereof with the corresponding 2,4'-isomer and 2,2'-isomer which process comprises:
heating said mixture of isomeric diamines with at least one mole, per mole of said 4,4'-diaminodiphenylmethane, of Bisphenol-A in the presence of an inert organic solvent;
separating from the reaction mixture the solid complex of Bisphenol-A and 4,4'-diaminodiphenylmethane so formed; and
treating said complex with an excess of dilute aqueous alkali solution to regenerate the substantially pure 4,4'-diaminodiphenylmethane therefrom.

9. The process of claim 8 wherein said mixture of isomeric diamines comprises a mixture of diamines and oligomeric polymethylene polyphenyl polyamines obtained by the condensation of aniline and formaldehye.

10. The 2:1 molar complex of phenol and 4,4'-diaminodiphenylmethane.

11. The 1:1 molar complex of Bisphenol-A and 4,4'-diamino diphenylmethane.

* * * * *